US008034371B2

(12) United States Patent
Castile et al.

(10) Patent No.: US 8,034,371 B2
(45) Date of Patent: Oct. 11, 2011

(54) INTRANASAL COMPOSITIONS

(75) Inventors: Jonathan David Castile, Nottingham (GB); Yu-Hui Cheng, Nottingham (GB); Paul George Jenkins, Nottingham (GB); Alan Smith, Nottingham (GB); Peter James Watts, Nottingham (GB)

(73) Assignee: Archimedes Development Limited, Nottingham (GB)

( * ) Notice: Subject to any disclaimer, the term of this patent is extended or adjusted under 35 U.S.C. 154(b) by 1016 days.

(21) Appl. No.: 10/596,817

(22) PCT Filed: Dec. 23, 2004

(86) PCT No.: PCT/GB2004/005446
§ 371 (c)(1),
(2), (4) Date: Mar. 1, 2007

(87) PCT Pub. No.: WO2005/060945
PCT Pub. Date: Jul. 7, 2005

(65) Prior Publication Data
US 2007/0140981 A1    Jun. 21, 2007

(30) Foreign Application Priority Data
Dec. 24, 2003 (GB) .................................. 0329918.7

(51) Int. Cl.
*A61K 9/08* (2006.01)
*A61K 9/12* (2006.01)
*A61K 31/44* (2006.01)
*A61F 13/00* (2006.01)

(52) U.S. Cl. .......... 424/434; 424/45; 514/303; 514/219; 514/923

(58) Field of Classification Search .................. 424/434, 424/45; 514/303, 219, 923
See application file for complete search history.

(56) References Cited

U.S. PATENT DOCUMENTS

| 5,655,517 A | 8/1997 | Coffee |
| 6,699,849 B1 * | 3/2004 | Loftsson et al. ................ 514/58 |
| 6,713,461 B1 | 3/2004 | Billotte |
| 7,423,026 B2 | 9/2008 | Jarvinen et al. |
| 2004/0176359 A1 | 9/2004 | Wermeling |
| 2004/0241100 A1 | 12/2004 | Kramer et al. |
| 2005/0215520 A1 * | 9/2005 | Liu et al. .......................... 514/58 |

FOREIGN PATENT DOCUMENTS

| EP | 0 681 833 A2 | 11/1995 |
| EP | 1250925 | * 4/2002 |
| WO | 98/30207 A1 | 7/1998 |
| WO | 99/01498 A1 | 1/1999 |
| WO | WO 03080021 | * 10/2003 |
| WO | 03/095498 A1 | 11/2003 |
| WO | 2004/067004 A1 | 8/2004 |

OTHER PUBLICATIONS

Illum, "Nasal drug delivery: new developments and Strategies", Drug Discovery Today, vol. 7, No. 23, pp. 1184-1189, (2002).
Sweetman, "Martindale, The Complete Drug Reference", Pharmaceutical Press, 33rd Edition, pp. 712-713, (2002).
Scrip, No. 2976, pp. 22, (2004).
Merck Index, No. 10321, pp. 1739.
Clauss et al., "Transient Improvement of Spinocerebellar Ataxia With Zolpidem", New England Journal of Medicine, pp. 511-512, (2004).
Communication pursuant to Article 94(3) EPC, dated Apr. 7, 2008, in European Application No. 04 806 240.0, (related to U.S. Appl. No. 10/596,817) 5 pages.
Merkus et al., "Cyclodextrins in Nasel Drug Delivery"; Advaned Drug Delivery Reviews, 36th Edition, pp. 41-57, (1999).
Illum, "Nasel Delivery. The Use of Animal Models to Predict Performance in Man"; Journal of Drug Targeting, vol. 3, pp. 427-442 (1996).
Dollery, "Therapeutic Drugs", Churchill Livingstone, 2nd Edition, pp. Z18-Z26, (1999).
Thompson, "Cyclodextrins Enabling Excipients: Their Present and Future Use in Pharmaceuticals", Critical Reviews in Therapeutic Drug Carrier Systems, vol. 14, pp. 1-104, (1997).
Florence et al., "Physicochemical Principles of Pharmacy", Macmillan, London, 3rd Edition, pp. 357-360, (1998).
Martin et al., "Physical Chemical Principles in the Pharmaceutical Sciences", Physical Pharmacy, Fourth Edition, pp. 516-519, (1993).
Gennaro, "Remington: The Science and Practice of Pharmacy", 20th Edition, Chapter 37, pp. 681-699, (2000).
Carstensen, "Pharmaceutical Principles of Solid Dosage Forms", Technomic, pp. 15-31 & 95-104, (1993).

* cited by examiner

*Primary Examiner* — Mina Haghighatian
(74) *Attorney, Agent, or Firm* — Panitch Schwarze Belisario & Nadel LLP

(57) ABSTRACT

The present invention provides compositions for the intranasal administration of zolpidem or a pharmaceutically acceptable salt thereof. Preferred compositions of the invention are in the form of aqueous solutions. Optionally the compositions of the invention comprise a cyclodextrin and/or chitosan, a salt or derivative thereof or a salt of a derivative of chitosan. The compositions can be used for the treatment or prevention insomnia or the treatment of neurological disorders such as those arising from brain trauma, stroke and spinocerebellar ataxia or in the treatment of Parkinson's disease.

10 Claims, 2 Drawing Sheets

*Figure 1. Solubility of zolpidem tartrate in solutions containing SBE-CD and SBE-CD + chitosan (lines of best fit shown)*
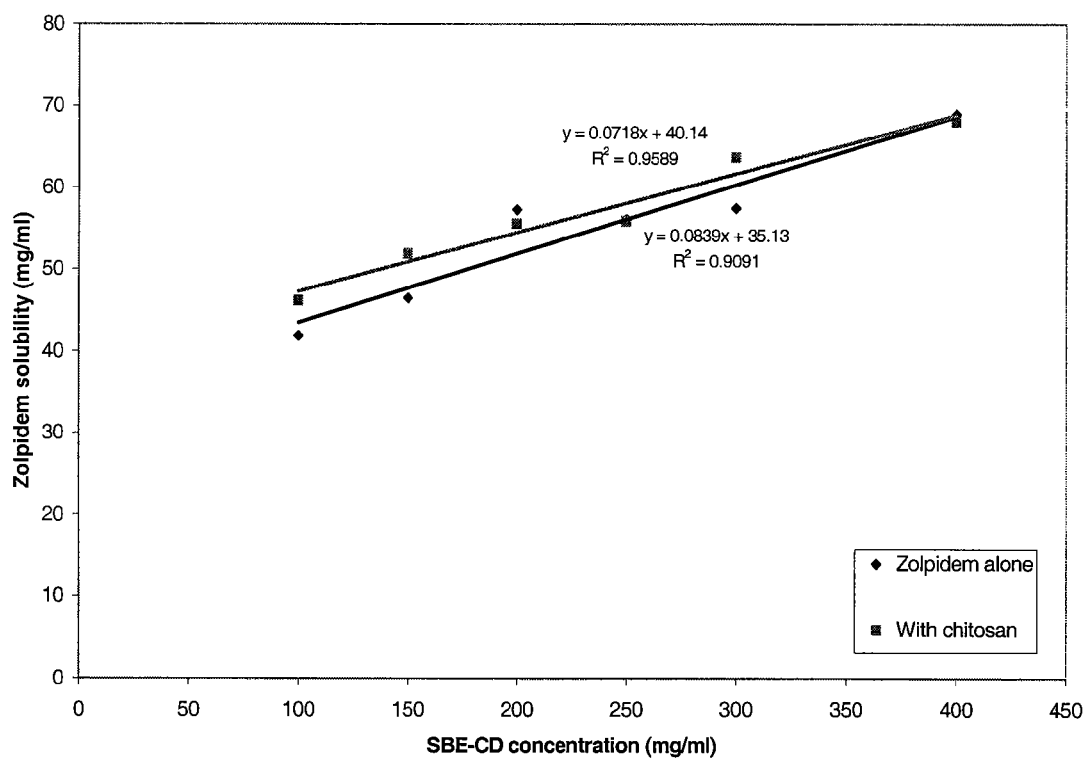

Figure 2. *Plasma concentration curves following administration of intravenous and intranasal zolpidem formulations to sheep (mean of five animals)*
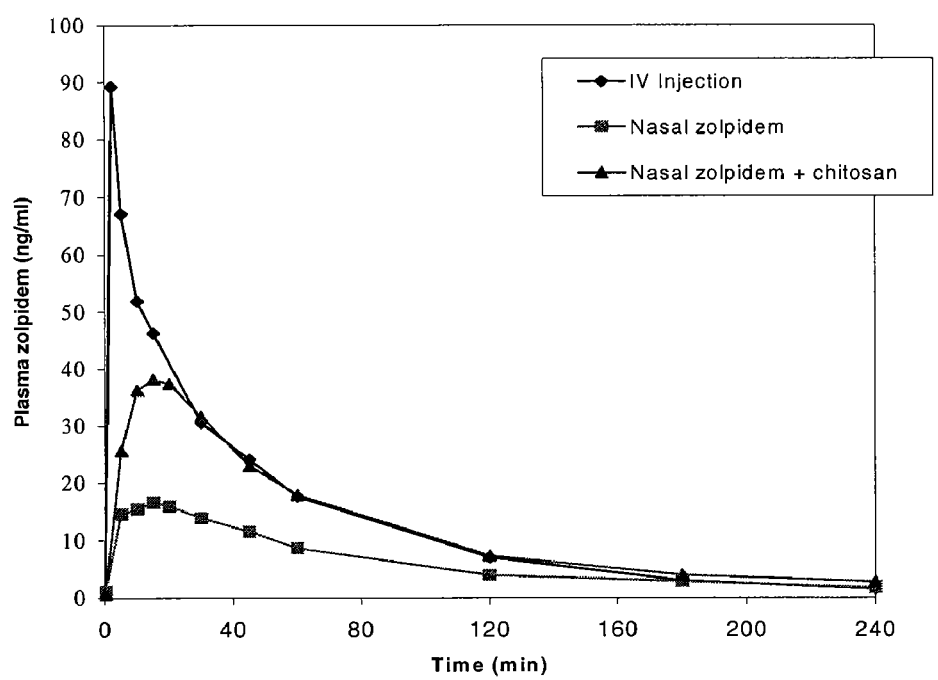

INTRANASAL COMPOSITIONS

CROSS-REFERENCE TO RELATED APPLICATIONS

This application is a Section 371 of International Application No. PCT/GB2004/005446, filed Dec. 23, 2004, which was published in the English language on Jul. 7, 2005, under International Publication No. WO 2005/060945 A2 and the disclosure of which is incorporated herein by reference.

This invention relates to pharmaceutical compositions for the intranasal administration of the compound zolpidem and its pharmaceutically acceptable salts.

Zolpidem (molecular weight 307.4) is N,N,6-trimethyl-2-(4-methylphenyl)-imidazo[1,2-a]pyridine-3-acetamide and has the following structure.

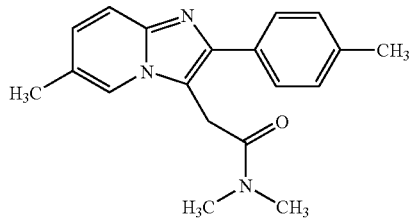

Zolpidem binds in the central nervous system to $GABA_a$ receptors containing the $a_1$, subunit and its principal therapeutic use is as a sedative/hypnotic used therapeutically for the short-term management of insomnia (see pages Z18-Z27, Therapeutic Drugs, Dollery (ed), $2^{nd}$ edition, Churchill Livingstone, Edinburgh, 1999).

However, zolpidem has also been reported to have other potential therapeutic applications. For example, zolpidem may be of use in treating neurological disorders such as those arising from brain trauma, stroke and spinocerebellar ataxia. In such neurological conditions zolpidem may be able to restore functions such as speech, movement and recognition (Scrip, No. 2976, p. 22, 2004; Clauss R, Sathekge M and Nel W, N. Engl. J Med., 351 (5), 511-512, 2004). Zolpidem may also be of benefit in improving the symptoms of Parkinson's disease (Martindale, $33^{rd}$ edition, p. 713, Pharmaceutical Press, London, 2002).

Zolpidem is typically administered therapeutically as the tartrate salt (MW 764.8). The adult dose is typically 10 mg (5 mg in elderly) by the oral route.

The present inventors have found that the intranasal route of administration can be advantageous for zolpidem and can offer significant benefits compared with administration via the oral route. In particular, it has been found that peak plasma concentrations can be reached much more rapidly when zolpidem is administered intranasally than when it is administered orally. Hence the nasal route can provide a more rapid onset of the therapeutic effects of zolpidem.

The present invention provides a composition for nasal delivery comprising zolpidem or a pharmaceutically acceptable salt thereof.

Zolpidem may be used as the free base or in the form of a pharmaceutically acceptable salt. Suitable pharmaceutically acceptable salts include, but are not limited to, the hydrochloride, mesilate, citrate, nitrate, lactate, maleate, tartrate, phosphate, succinate, fumarate and gluconate salts. Preferably zolpidem tartrate is used. It should be noted that zolpidem forms a "hemi" salt with tartaric acid in that the ratio of zolpidem to tartrate molecules is 2:1.

When producing a composition containing a salt of zolpidem, the appropriate salt may be used or zolpidem base may be dissolved in situ in a suitable acid.

The composition may be in any form suitable for nasal delivery. Suitable forms include aqueous or non-aqueous solutions and powders.

In one aspect, the present invention provides an aqueous solution comprising zolpidem or a pharmaceutically acceptable salt thereof, which is suitable for nasal delivery.

The aqueous solutions of the present invention preferably comprise zolpidem or a pharmaceutically acceptable salt thereof in a concentration of from 0.8 to 97 mg/ml (expressed as free base), more preferably from 4 to 80 mg/ml. Hence, when zolpidem is used in the form of the tartrate salt, the concentration of zolpidem tartrate is preferably from 1 to 120 mg/ml, more preferably from 5 to 100 mg/ml.

The concentration of zolpidem in the solutions of the present invention will depend, at least to some extent, on the intended therapeutic use.

When the solutions are intended to be used to prevent or treat insomnia the aqueous solutions of the present invention preferably comprise zolpidem or a pharmaceutically acceptable salt thereof in a concentration of from 16 to 97 mg/ml (expressed as free base), more preferably from 20 to 90 mg/ml and most preferably from 24 to 80 mg/ml. Hence, when zolpidem is used in the form of the tartrate salt, the concentration of zolpidem tartrate is preferably from 20 to 120 mg/ml, more preferably from 25 to 110 mg/ml and most preferably from 30 to 100 mg/ml. As used herein, compositions containing a concentration of zolpidem within these ranges are referred to as "higher concentration compositions or solutions" or "compositions or solutions intended for use in the treatment of insomnia".

The reported aqueous solubility of zolpidem tartrate is 23 mg/ml (Merck Index). However, these values typically represent the saturated solubility of the drug and concentrations achievable in practical pharmaceutical formulations are typically lower. It is therefore preferable that the solutions of the present invention include a means of enhancing zolpidem aqueous solubility. Although it has been found that the solubility of zolpidem tartrate may be increased by reducing the pH i.e. by the addition of acid, this approach is typically only of value in producing solutions suitable for intranasal administration containing relatively low concentrations of zolpidem, such as less than 20 mg/ml. A solubility enhancing agent (other than an acid) is preferably used in the solutions of the invention, especially in solutions containing in excess of 20 mg/ml of zolpidem.

By the term "solubility enhancing agent" we mean a water-soluble ingredient (having a solubility in water of 10 mg/ml or greater) that, in the presence of zolpidem or a pharmaceutically acceptable salt thereof is able to increase the amount of zolpidem or salt that can dissolve. Thus, when zolpidem or a pharmaceutically acceptable salt is added to an aqueous solution containing the solubility enhancing agent, the amount of zolpidem or salt that will dissolve is higher than when zolpidem or salt is added to water only.

Suitable solubility enhancing agents include, but are not limited to poloxamers, polyethylene glycols, benzyl alcohol and cyclodextrins. Preferably, the solubility enhancing agent is a cyclodextrin.

Cyclodextrins are oligosaccharides made up of glucopyranose units and produced by the enzymatic degradation of starch. They are "bucketlike" or "conelike" toroid molecules with a rigid structure and a central cavity, the size of which varies according to the cyclodextrin type. The internal cavity of cyclodextrins is hydrophobic and may allow for the inclusion of lipophilic molecules, thus improving the aqueous solubility of poorly soluble drugs (Thompson, Crit. Rev. Ther. Drug Carr. Sys., 14, 1-104, 1997).

The three major types of cyclodextrin (CD) are ($\alpha$, $\beta$ and $\gamma$ which comprise 6, 7 and 8 glucopyranose units respectively. To extend their usefulness as pharmaceutical excipients, CDs, in particular $\beta$-CD, have been chemically modified, for example to produce derivatives that have enhanced aqueous solubility. Such derivatives include but are not limited to carboxymethyl-$\beta$-CD, carboxymethyl-ethyl-$\beta$-CD, diethyl-$\beta$-CD, methyl-$\beta$-CD, dimethyl-$\beta$-CD, trimethyl-$\beta$-CD, randomly methylated-$\beta$-CD, glucosyl-$\beta$-CD, maltosyl-$\beta$-CD, hydroxyethyl-$\beta$-CD, 2-hydroxypropyl-$\beta$-CD and sulfobutylether-$\beta$-CD.

The preferred cyclodextrins for use in the present invention are $\alpha$-CD, $\beta$-CD, $\gamma$-CD and the modified derivatives of $\beta$-CD, such as 2-hydroxypropyl-$\beta$-CD, randomly methylated $\beta$-CD and sulfobutylether-$\beta$-CD. Especially preferred cyclodextrins are $\gamma$-CD, 2-hydroxypropyl-$\beta$-CD, randomly methylated $\beta$-CD and sulfobutylether-$\beta$-CD (SBE-CD). Suppliers of $\gamma$-CD, hydroxypropyl-$\beta$-CD and randomly methylated $\beta$-CD include ISP (Wayne, N.J., USA), Roquette (Lestrem, France) and Cerestar (Mechelen, Belgium). SBE-CD can be obtained from CyDex Inc (Lenexa, Kans., USA) under the trade name Captisol®.

The most preferred cyclodextrin for use in the solutions of the present invention is sulfobutylether-$\beta$-CD (SBE-CD).

If the solutions of the invention comprise a cyclodextin, the cyclodextrin is preferably present in an amount of from 50 to 700 mg/ml, more preferably from 75 to 500 mg/ml and most preferably from 100 to 400 mg/ml.

For the treatment of neurological disorders it has been suggested that the zolpidem dose used in treating insomnia (10 mg) may be associated with unwanted drowsiness and that smaller doses may be appropriate (Scrip, No. 2976, p. 22, 2004). Drowsiness has also been identified as an issue in using zolpidem to treat the symptoms of Parkinson's disease (Martindale, 33$^{rd}$ edition, p. 713, Pharmaceutical Press, London, 2002). Hence, although the intranasal solution compositions described for treating insomnia may also be suitable for use in treating conditions such as Parkinson's disease and neurological disorders, it may be desirable to use, lower, less sedating doses of zolpidem. A lower dose can be provided by a lower volume of a solution comprising zolpidem in a concentration suitable for the prevention or treatment of insomnia or an appropriate quantity of the powder compositions. Alternatively, solutions containing a lower concentration of zolpidem could be used.

For example, such lower concentration zolpidem compositions may contain from 0.8 to 20 mg/ml zolpidem, more preferably from 1.6 to 18 mg/ml zolpidem and most preferably from 2.4 to 16 mg/ml zolpidem. These zolpidem tartrate concentrations are equivalent to from 1 to 25 mg/ml zolpidem tartrate, from 2 to 23 mg/ml zolpidem tartrate and from 3 to 20 mg/ml zolpidem tartrate, respectively. As used herein, compositions containing a concentration of zolpidem within these ranges are referred to as "lower concentration compositions or solutions" or "compositions or solutions intended for use in the treatment of neurological disorders". Compositions containing these concentrations of zolpidem may be prepared without the inclusion of a solubility enhancing agent, such as a cyclodextrin.

The aqueous solutions of the invention preferably have a pH of from 3 to 8. When the solutions contain zolpidem in an amount defined above as preferred for solutions intended to be used to prevent or treat insomnia the pH is more preferably from 3.5 to 7.5 and most preferably from 4.0 to 7.0.

The pH of the solutions may be adjusted to the desired value using any suitable organic or inorganic acid or organic or inorganic base. Suitable organic acids include, but are not limited to, acetic acid, citric acid, glutamic acid and methane sulfonic acid. Suitable inorganic acids include, but are not limited to, hydrochloric acid and sulphuric acid. Suitable organic bases include, but are not limited to, meglumine, lysine and tromethamine (TRIS). Suitable inorganic bases include, but are not limited to, sodium hydroxide and potassium hydroxide. Alternatively, or in addition, a buffer system may be included in the compositions in order to adjust and maintain pH. Examples of suitable buffer systems include, but are not limited to, a phosphate buffer comprising disodium hydrogen phosphate and potassium dihydrogen phosphate, and a citrate buffer comprising sodium citrate and citric acid.

Lower concentration solutions may be prepared, for example, by dispersing an appropriate quantity of zolpidem tartrate in water (or optionally aqueous chitosan solution), adding sufficient acid, such as hydrochloric acid to dissolve the drug compound, adjusting the pH as necessary with a base, making the solution isotonic, for example by adding sodium chloride, and making to volume with water. The pH of these lower concentration zolpidem tartrate compositions is preferably from 3.0 to 5.0, more preferably from 3.2 to 4.8 and most preferably from 3.4 to 4.6.

The aqueous solutions of the invention may additionally comprise chitosan, a salt or derivative of chitosan or salt of a derivative of chitosan.

Chitosan is a cationic biopolymer comprising glucosamine and N-acetyl glucosamine that has bioadhesive properties and has been shown to improve the systemic bioavailability of certain drug compounds across mucosal surfaces such as the nasal cavity (see *Illum, Drug Discovery Today*, 7, 1184-1189, 2002).

By the term "chitosan" we include all derivatives of chitin, or poly-N-acetyl-D-glucosamine, including all polyglucosamines and oligomers of glucosamine materials of different molecular weights, in which the greater proportion of the N-acetyl groups have been removed through hydrolysis (deacetylation). In accordance with the present invention, the degree of deacetylation, which represents the proportion of N-acetyl groups which have been removed through deacetylation, should preferably be in the range 40-97%, more preferably in the range 60-96% and most preferably be in the range 70-95%.

The chitosan, chitosan derivative or salt used in the present invention should preferably have a molecular weight in the range 10,000 to 1,000,000 Da, more preferably in the range 15,000 to 750,000 Da and most preferably in the range 20,000 to 500,000 Da.

Salts of chitosan are suitable for use in the present invention. Salts with various organic and inorganic acids are suitable. Such suitable salts include, but are not limited to the nitrate, phosphate, glutamate, lactate, citrate, hydrochloride and acetate salts. Preferred salts are the hydrochloric acid and glutamic acid salts.

Chitosan derivatives and their salts are also suitable for use in this invention. Suitable chitosan derivatives include, but are not limited to, esters, ethers or other derivatives formed by bonding acyl and/or alkyl groups with the hydroxyl groups, but not the amino groups of chitosan. Examples include O-alkyl ethers of chitosan and O-acyl esters of chitosan. Modified chitosans, such as those conjugated to polyethylene glycol may be used in the present invention. Conjugates of chitosan and polyethylene glycol are described in WO99/01498.

Chitosans suitable for use in the present invention may be obtained from various sources, including Primex, Haugesund, Norway; NovaMatrix, Drammen, Norway; Seigagaku America Inc., MD., USA; Meron (India) Pvt, Ltd., India; Vanson Ltd, VA., USA; and AMS Biotechnology Ltd., UK. Suitable derivatives include those that are disclosed in Roberts, Chitin Chemistry, MacMillan Press Ltd., London (1992).

Particularly preferred chitosan compounds that may be mentioned include chitosan glutamate (available as Protasan UPG213 from NovaMatrix, Drammen, Norway).

The concentration of chitosan in the aqueous solutions is preferably from 0.5 to 50 mg/ml, more preferably from 0.75 to 35 mg/ml and most preferably from 1 to 20 mg/ml.

Solutions containing a lower concentration of zolpidem and solutions containing a higher concentration of zolpidem preferably contain chitosan.

A preferred aqueous solution containing a higher concentration of zolpidem suitable, for example for treating insomnia, comprises from 30 to 60 mg/ml of zolpidem tartrate, from 100 to 300 mg/ml SBE-CD and from 2 to 10 mg/ml of chitosan glutamate.

A preferred aqueous solution containing a lower concentration of zolpidem suitable, for example, for treating neurological disorders or Parkinson's disease comprises from 3 to 20 mg/ml of zolpidem tartrate, and from 2 to 10 mg/ml of chitosan glutamate and preferably has a pH of from 3.4 to 5.0.

The aqueous solutions containing chitosan, a salt or derivative thereof or a salt of a chitosan derivative preferably have a pH of from 3 to 6, more preferably from 3.2 to 5.8 and most preferably from 3.5 to 5.6. Lower pHs such as pHs of 5.0 or below are preferred if the solution does not comprise a solubility enhancing agent (other than an acid). The pH of the chitosan containing solutions may be adjusted as described earlier although it is preferred not to use citrate salts as the use of citrate salts can result in precipitate formation in the presence of chitosan.

The viscosity of the aqueous solutions of the present invention is preferably less than 250 centipoise (cp), more preferably less than 200 cp and most preferably less than 150 cp.

Surprisingly, the present inventors have found that the use of chitosan, a salt or derivative thereof or a salt of a derivative of chitosan increases the extent of intranasal absorption of zolpidem in the form of a complex with SBE-CD. By "increased extent of absorption", we mean that the maximum plasma concentration ($C_{max}$) and bioavailability are higher compared to a composition that contains no chitosan and given at the same zolpidem dose.

The water used to prepare the solutions of the present invention can be boiled and cooled and/or purged with a gas such as helium in order to minimise the dissolved oxygen content and hence maximise drug stability. Purified water such as water for injections may be used in the compositions of the present invention.

The compositions of the invention may, alternatively, be in the form of a non-aqueous solution or a powder composition.

Solvents that may be used to prepare the non-aqueous solutions of the invention include, but are not limited to ethanol, propylene glycol, polyethylene glycol, glycofurol, benzyl benzoate and polyoxyethylene castor oil derivatives, such as Cremophor® (BASF, Germany). The concentration of zolpidem in the non-aqueous solutions of the invention is typically as described above for the aqueous solutions.

The solutions of the present invention may also contain other pharmaceutically acceptable ingredients well known in the art. Such ingredients include, but are not limited to, antioxidants (for example sodium metabisulphite), chelating agents (such as edetic acid or one of its salts), preservatives (such as potassium sorbate, parabens, phenylethyl alcohol or benzalkonium chloride), flavours, sweeteners, thickening, adhesive or gelling agents, including, but not limited to, celluloses such as hydroxypropyl methylcellulose, methylcellulose, hydroxypropyl cellulose, sodium carboxyl cellulose and microcrystalline cellulose, poloxomers, polyethylene glycols, carbomers or polyethylene oxide.

Preferably the solutions of the invention contain a preservative and/or are sterile. If preservatives are omitted from the compositions, microorganisms may be removed using any suitable method known in the art, for example by making the compositions aseptically or by terminally sterilising them.

Preferably the compositions of the invention are non-pyrogenic.

Methods of formulating drug substances for administration in a powder form are well known to those skilled in the art. For example, the powder formulations of the present invention may be in the form of a blend of drug powder with other ingredients, as granules or as microspheres.

The powder compositions of the present invention may comprise a cyclodextrin. Suitable cyclodextrins are described above. The most preferred cyclodextrin for use in the powder compositions is SBE-CD. The present inventors have surprisingly found that cyclodextrins can enhance the rate of drug dissolution from the powder compositions into the nasal cavity.

When the powder compositions of the present invention comprise a cyclodextrin, the cyclodextrin may be incorporated into the powder blend, granules or microspheres in solid (powder) form. Alternatively, the zolpidem or salt thereof may be partially or completely pre-dissolved in an aqueous cyclodextrin solution and the water then removed to produce zolpidem-cyclodextrin inclusion complex in solid form. Suitable methods for removal of water from such a solution include spray drying, freeze-drying, vacuum drying and oven drying.

A powder blend according to the present invention may be prepared by mixing zolpidem or a pharmaceutically acceptable salt thereof with inert ingredients that are standard in the art. Such inert ingredients include, but are not limited to diluents such as calcium phosphate, lactose, sugars such as dextrose and sucrose, polyols such as mannitol and sorbitol, and microcrystalline cellulose, glidants such as colloidal silica and lubricants such as magnesium stearate and hydrogenated vegetable oil and surfactants such as polysorbates; and polyethylene glycol. The powder blend may optionally contain chitosan, a salt or derivative or a salt of a derivative of chitosan.

For preparing a uniform powder blend on a small scale, a pestle and mortar and/or sieve may be appropriate whereas mechanical mixers are required for larger scale manufacture. There are numerous types of mixer available and these are widely described in the literature, for example Chapter 37, Remington: The Science and Practice of Pharmacy, $20^{th}$ Edition, Lipincott, Williams and Wilkins, Baltimore, 2000.

Alternative processes for preparing the formulations of the invention include spray drying, granulation and supercritical fluid processes.

If the powder composition of the invention comprises granules, these granules may be produced by techniques well known to those skilled in the art such as wet granulation, dry granulation (slugging), extrusion/spheronisation, fluid bed granulation and spray congealing. Further details on granulation processes may be found in the literature, for example Chapter 6, Pharmaceutical Principles of Solid Dosage Forms, J. T. Carstensen, Technomic, Lancaster, Pa., 1993.

In addition to zolpidem or a pharmaceutically acceptable salt thereof, other ingredients may be incorporated into the granules. Such other ingredients include, but are not limited to diluents such as calcium phosphate, lactose, dextrose, mannitol and microcrystalline cellulose, binders such as povidone (polyvinylpyrrolidone), methylcellulose, polyethylene glycol, gelatin and acacia, disintegrants such as starch, croscarmellose and crospovidone, glidants such as colloidal silica, and lubricants such as magnesium stearate and hydrogenated vegetable oil. The granules may optionally contain chitosan, a salt or derivative or a salt of a derivative of chitosan.

Methods for preparation of microspheres are well known to those skilled in the art and include, but are not limited to, spray drying, interfacial polymerisation, coarcervation/phase separation and solvent evaporation. Methods for producing microspheres are described in, for example, Physicochemical Principles of Pharmacy, $3^{rd}$ Edition, pages 357 to 360, A T Florence and D Attwood, Macmillan, London, 1998 and Physical Pharmacy, $4^{th}$ Edition, pages 516 to 519, A Martin, Wilkins and Wilkins, Baltimore, 1993. The microspheres may alternatively be produced using the methods described in WO98/30207 and the documents cited therein.

In addition to zolpidem or a pharmaceutically acceptable salt thereof, the microspheres used in the present invention may include ingredients that are known in the art to be suitable to be included in microspheres such as, but not limited to, starches, dextrans, gelatin, albumin, collagen, hyaluronic acid, chitosan, lactose, sucrose, dextrose, mannitol, methacrylate copolymers such as the Eudragit® polymers (Degussa, Germany), celluloses such as methylcellulose, and polyesters such as poly(lactide-co-glycolide).

The powder formulations of the present invention preferably have a zolpidem content of from 10 to 90% by weight (calculated as the free base), more preferably in the range 15 to 80% by weight and most preferably in the range 20 to 70% by weight.

If the powder formulations of the present invention comprise cyclodextrin, the ratio by weight of zolpidem or a pharmaceutical acceptable salt thereof (calculated as the free base) to cyclodextrin is preferably from 1:0.25 to 1:10, more preferably from 1:0.5 to 1:8 and most preferably from 1:1 to 1:7.

If the powder formulations of the present invention comprise chitosan, a salt or derivative or a salt of a derivative thereof, they preferably have a chitosan content from 1 to 70% by weight, more preferably in the range 2 to 60% and most preferably in the range 5 to 50%.

The powder formulations of the invention preferably have a particle size in the range of from 10 to 900 μm, more preferably from 10 to 600 μm and most preferably from 10 to 300 μm. More specifically, the mean particle size, expressed as the volume mean diameter ($D_{50\%}$) and measured by a technique such as light microscopy combined with image analysis lies within these ranges. The $D_{50\%}$ is preferably from 25 to 700 μm, more preferably from 25 to 450 μm and most preferably from 25 to 200 μm. Furthermore, no more than 10% by volume of the particles have a diameter ($D_{10\%}$) less than 10 μm and at least 90% by volume of the particles have a diameter ($D_{90\%}$) that does not exceed the upper limit of the size range.

It is desirable that the formulations of the invention do not contain substantial numbers of particles having a size below 10 μm in order to minimise the possibility of delivery into the lungs.

The compositions of the invention may be administered to the nasal cavity in any suitable form. For example, the solutions of the invention may be administered to the nasal cavity in the form of drops or a spray and the powders of the invention may be administered in aerosolised form.

A preferred method of administering the solutions of the invention is using a spray device. Spray devices can be single ("unit") dose or multiple dose systems, for example comprising a bottle, pump and actuator, and are available from various commercial sources, including Pfeiffer (Germany), Valois (France), Calmar (Germany), Ursatech (Germany), Bespak (UK) and Becton-Dickinson (USA). Electrostatic spray devices, such as described in U.S. Pat. No. 5,655,517, are also suitable for the intranasal administration of the solutions of the invention.

For a spray device, the typical volume of liquid that is dispensed in a single spray actuation is from 0.01 to 0.14 ml, for example from 0.05 to 0.14 ml, such as 0.1 ml. It is a practical proposition to administer up to about 0.2 ml into each nostril (i.e. two×0.1 ml sprays) to provide a therapeutic dose of drug, although the most acceptable dosing regimen would be one spray into one or both nostrils. On the basis of administering a zolpidem tartrate dose of 10 mg as a total of one or two 0.1 ml sprays to each nostril, the drug concentration is preferably from 50 to 100 mg/ml zolpidem tartrate. Obviously, the amount of zolpidem to be administered and/or the volume of liquid to be administered can be altered by changing the concentration of zolpidem in the solutions of the invention. For example, smaller spray volumes (or larger drug doses) could be administered if there was a corresponding increase in drug concentration i.e. a 10 mg dose could be administered as a single 0.14 ml spray of a 71 mg/ml zolpidem tartrate solution or 0.28 ml of a 36 mg/ml zolpidem tartrate solution.

The powder formulations of the present invention are preferably administered to the patient in aerosolised form whereby energy from patient inhalation (sniffing) is used to aerosolise the powder into the nasal cavity or where the device itself provides the aerosolisation energy, such as via compressed air. An example of the former device is manufactured by Pfeiffer and an example of the latter is the "Monopowder" manufactured by Valois.

The present invention also provides a nasal drug delivery device or a dose cartridge for use in a nasal delivery device loaded with a composition as defined above.

The present invention also provides processes for preparing the compositions of the invention. The process for preparing the solutions of the invention comprises mixing the components in a suitable solvent such as water. The powder compositions may be prepared using methods known in the art.

The compositions of the present invention have sleep-inducing properties and may be used in the treatment and/or prevention of insomnia. The compositions of the invention may alternatively be used in the treatment of neurological disorders such as those arising from brain trauma, stroke and spinocerebellar ataxia or in the treatment of Parkinson's disease. Thus, the present invention provides a method of administering zolpidem to a patient in need thereof, for example for the prevention or treatment of insomnia or the treatment of neurological disorders such as those arising from brain trauma, stroke and spinocerebellar ataxia or the treatment of Parkinson's disease, which comprises the intranasal administration of a composition as defined above to the patient.

The present invention also provides the use of zolpidem or a pharmaceutically acceptable salt thereof in the manufacture of a medicament for nasal administration to a patient in need thereof. Such a medicament may have sleep-inducing properties and may be used in the treatment and/or prevention of insomnia. Alternatively it may be used in the treatment of neurological disorders such as those arising from brain trauma, stroke and spinocerebellar ataxia or in the treatment of Parkinson's disease.

In the Figures:

FIG. 1 shows the solubility of zolpidem tartrate in solutions containing SBE-CD and SBE-CB with chitosan.

FIG. 2 shows plasma concentration curves following administration of intravenous and intranasal zolpidem formulations to sheep.

The invention is illustrated by the following non-limiting examples.

EXAMPLE 1

Solubility of Zolpidem Tartrate in Different Cyclodextrins

A semi-quantitative comparison was made of the ability of different cyclodextrins to enhance the aqueous solubility of zolpidem tartrate.

Aqueous solutions were prepared containing 200, 300 and 400 mg/ml of three types of cyclodextrin. These were hydroxypropyl-β-cyclodextrin (HP-CD) (Cavamax® W7 HP Pharma, Wacker, Germany), methylated-β-cyclodextrin (M-CD) (Cavamax® W7 M Pharma, Wacker) and sulfobutylether-β-cyclodextrin (SBE-CD) (Captisol®, CyDex, USA). 25 mg samples of zolpidem tartrate (ZMC, Zheijang, Hangzhou, China) were added to a 0.5 ml portion of each cyclodextrin solution. The mixtures (containing 50 mg/ml drug) were stirred overnight at room temperature. If drug dissolved then more was added. If undissolved drug remained then an additional 0.5 ml of cyclodextrin solution was added and stirring continued. From this experiment an estimate could be made of zolpidem tartrate solubility in the different cyclodextrin solutions. Results are summarised in Table 1.

TABLE 1

Comparison of zolpidem solubility in different cyclodextrins

| CD concentration | Zolpidem tartrate solubility in CD (mg/ml) | | |
| --- | --- | --- | --- |
| | HP-CD | M-CD | SBE-CD |
| 200 | 25-31 | 25-31 | >50 |
| 300 | 31-36 | 31-36 | 50-56 |
| 400 | 36-50 | 31-36 | ~60 |

All cyclodextrins tested enhanced the aqueous solubility of zolpidem tartrate. Of the cyclodextrins tested, SBE-CD was the most effective at enhancing the aqueous solubility of zolpidem tartrate.

EXAMPLE 2

Solubility of Zolpidem Tartrate in SBE-CD

The experiment described in Example 1 indicated that zolpidem tartrate solubility was highest in SBE-CD. Based on this result a more accurate determination of solubility in SBE-CD was performed, as follows:

A stock solution was prepared containing 400 mg/ml SBE-CD in water and then dilutions made to 100, 150, 200, 250 and 300 mg/ml. Into 2 ml portions of the stock and diluted SBE-CD solutions was dissolved 10 mg of chitosan glutamate (Protasan UPG213, NovaMatrix, Drammen, Norway). To each of these samples of SBE-CD/chitosan solution and to each of six chitosan-free 2 ml samples of SBE-CD solutions were added 140 mg samples of zolpidem tartrate. The samples were left to stir overnight at room temperature (18° C.). If during this time all the drug dissolved, further amounts were added until a suspension was formed (i.e. saturated drug solution formed). After further stirring for up to 72 hours, suspensions were filtered (0.45 μm filter, Gelman, Portsmouth, UK) to recover saturated zolpidem tartrate solutions. The filtrate samples were diluted in water and the UV absorbance at 296 nm measured. By reference to a calibration curve of UV absorbance (296 nm) vs. zolpidem concentration, the concentration of zolpidem in the samples was calculated. Solubility data are presented in Table 2 and presented graphically in FIG. 1.

TABLE 2

Zolpidem solubility in SBE-CD solutions with and without chitosan

| SBE-CD conc (mg/ml) | Zolpidem tartrate solubility (mg/ml) | Zolpidem tartrate solubility in presence of 5 mg/ml chitosan glutamate (mg/ml) |
| --- | --- | --- |
| 100 | 41.9 | 46.2 |
| 150 | 46.5 | 51.9 |
| 200 | 57.3 | 55.6 |
| 250 | 56.1 | 55.9 |
| 300 | 57.5 | 63.7 |
| 400 | 69.0 | 68.1 |

The data indicate that the enhancement of zolpidem tartrate solubility by SBE-CD appears to be relatively linear over the SBE-CD concentration range of 100-400 mg/ml. Chitosan appeared not to affect zolpidem solubility.

EXAMPLE 3

Intranasal Solution Containing 50 mg/mil Zolpidem Tartrate and 200 mg/ml SBE-CD 300 mg of 50% benzalkonium chloride solution (Albright & Wilson, Whitehaven, UK) was weighted into a 10 ml volumetric flask and 8 ml of water for injection added. The flask contents were stirred to disperse the benzalkonium chloride and then made up to volume with water. This produced a stock solution containing 15 mg/ml benzalkonium chloride.

5 g of SBE-CD was weighed into a 25 ml volumetric flask and dissolved by adding approximately 15 ml of water followed by stirring. 1.25 g of zolpidem tartrate was added to the volumetric flask together with an additional 5 ml of water and 0.25 ml of 15 mg/ml benzalkonium chloride stock solution. The solution was adjusted to approximately pH 4.5 by the addition of 0.1M hydrochloric acid solution (prepared by dilution of concentrated hydrochloric acid (Fisher)) and then made up to 25 ml with water. The solution was passed through a 0.45 μm membrane filter (Sartorius, Leicester, UK) and the pH measured. The final solution was at pH 4.6.

EXAMPLE 4

Intranasal Solution Containing 50 mg/ml Zolpidem Tartrate, 200 mg/ml SBE-CD and 5 mg/ml Chitosan Glutamate 10 g of SBE-CD and 250 mg of chitosan glutamate (Protasan UPG213, NovaMatrix, Drammen, Norway) were weighed and transferred into a 50 ml volumetric flask and dissolved by adding approximately 30 ml of water followed by stirring. 2.5 g of zolpidem tartrate was added to the volumetric flask together with an additional 10 ml of water and 0.5 ml of 15 mg/ml benzalkonium chloride stock solution. The solution was adjusted to approximately pH 4.5 by the addition of 0.1M hydrochloric acid solution and then made up to 50 ml with water. The solution was passed through a 0.45 µm membrane filter (Sartorius, Leicester, UK) and the pH measured. The final solution was at pH 4.7.

EXAMPLE 5

Solution for Intravenous Injection Containing 1 mg/ml Zolpidem Tartrate and 8.9 mg/ml Sodium Chloride 50 mg of zolpidem tartrate was weighed into a 50 ml volumetric flask and dissolved by adding 40 mg of water. 445 mg of sodium chloride (Sigma, Poole, UK) was added to the volumetric flask and dissolved by stirring. The solution was made up to 50 ml by adding water. In a laminar flow cabinet the solution was sterile filtered (0.2 µm membrane filter) into sterile injection vials that were sealed with elastomeric closures and aluminium caps.

EXAMPLE 6

Pharmacokinetic Performance of Intranasal Zolpidem Formulations in Sheep

The pharmacokinetic performance of the intranasal and intravenous zolpidem solutions described in Examples 3 to 5 was evaluated in sheep.

A group of five female sheep was used, each weighing around 45 kg. The formulations were administered to a randomised cross-over design. Each intranasal formulation (Examples 3 and 4) was administered at a zolpidem dose of 20 mg. This dose was provided by transferring 3.5 ml of the test formulation into a glass bottle, attaching a Valois VP7 spray pump and actuator to the bottle, priming the pump and then administering two 0.1 ml sprays into each nostril. For the intravenous dose, 5 mg of zolpidem was administered as a 5 ml bolus of the injection prepared in Example 5.

Blood samples were collected over a 360 minute period following dosing and plasma separated. Plasma samples were assayed by an HPLC method for zolpidem content. Pharmacokinetic parameters were calculated from the plasma data.

A summary of pharmacokinetic parameters is provided in Table 3. Plasma concentration versus time curves are provided in FIG. 2.

The pharmacokinetic data indicate rapid absorption of zolpidem following intranasal administration ($T_{max}$ values of 13 and 16 minutes). In addition, the bioavailability was significantly enhanced by the inclusion of chitosan in the intranasal solution formulation.

EXAMPLE 7

Preparation of Zolpidem Tartrate/Chitosan Glutamate Powder Blend 5 g of zolpidem tartrate, 3 g of chitosan and 2 g of lactose (InhaLac® 120, Meggle, Germany) are weighed into a glass bottle. The lid is attached to the bottle, which is placed into a Turbula T2C mixer (Willy Bachofen, Bubendorf, Switzerland). The bottle contents are mixed at speed setting 2 for 30 minutes. A 10 mg sample of the powder blend is filled into a Monopowder nasal spray device (Valois, Marly-le-Roi, France). When actuated, this device will deliver 10 mg of powder, equivalent to 5 mg of zolpidem tartrate.

EXAMPLE 8

Preparation of Zolpidem Tartrate/SBE-CD/Chitosan Glutamate Powder Blend 12 g of SBE-CD is weighed into a 100 ml flask and dissolved in 30 ml of water. 6 g of zolpidem tartrate is added to the SBE-CD solution and stirred for 60 minutes. The resulting suspension is frozen in liquid nitrogen and freeze-dried for 72 hours. The freeze-dried product is passed through a 0.25 mm mesh size sieve and 15 g transferred to a glass bottle. 2.5 g of chitosan glutamate and 2.5 g of lactose (InhaLac® 120) are added to the bottle, which is sealed and placed into a Turbula T2C mixer. The bottle contents are mixed at speed setting 2 for 30 minutes. A 20 mg sample of the powder blend is filled into a Monopowder nasal spray. When actuated, this device will deliver 20 mg of powder, equivalent to 5 mg of zolpidem tartrate.

EXAMPLE 9

Intranasal Solutions Containing 10, 15 and 20 mg/ml Zolpidem Tartrate and 5 mg/ml Chitosan Glutamate A 10 mg/ml stock solution of chitosan glutamate (Protosan UPG213, Novamatrix, Drammen, Norway) was prepared by weighing 500 mg of chitosan glutamate into a 50 ml volumetric flask and making the flask contents up to volume using water.

Solutions containing 20, 15 and 10 mg/ml zolpidem tartrate (ZMC, Zheijang, China) were prepared by weighing duplicate 200 mg, 150 mg and 100 mg samples of zolpidem tartrate, respectively, into six 10 ml volumetric flasks. 5 ml of the 10 mg/ml chitosan glutamate solution was then added to each flask containing zolpidem tartrate. The contents were then stirred to disperse the zolpidem tartrate and an additional 4 ml of water added. 10 µl aliquots of 1.0 M hydrochloric acid were added until the solutions were clear followed by the

TABLE 3

Summary of pharmacokinetic parameters following administration of zolpidem intranasal and IV injection doses to sheep (mean, n = 5 [SD]).

| Dose group | $T_{max}$ (min) | $C_{max}$ (ng/ml) | AUC (ng/ml · min) | Absolute bioavailability (%) |
|---|---|---|---|---|
| Nasal solution (Example 3) | 13 [8] | 18 [3] | 1328 [544] | 10 [4] |
| Nasal solution + 5 mg/ml chitosan (Example 4) | 16 [5] | 40 [11] | 2822 [786] | 22 [6] |
| IV injection (Example 5) | 0 [0] | 109 [28] | 3298 [684] | 100 | addition of 10 µl aliquots of 1.0 M sodium hydroxide solution to bring the solutions to the required pH (pH 4.0 or 3.5). Each solution was then made up to volume with water.

The solutions were stored refrigerated (2-8° C.) for two weeks to observe if any precipitation of drug occurred. The results are presented in Table 4.

Formulations containing zolpidem tartrate at a concentration of 20 mg/ml and 15 mg/ml at pH 4.0 were found to contain a white precipitate when stored refrigerated for two weeks. All the other formulations remained clear, colourless solutions. Hence, it is possible to prepare physically stable solutions containing 10-20 mg/ml zolpidem tartrate without the use of an additional solubilising agent, such as a cyclodextrin. For solutions containing 15-20 mg/ml zolpidem tartrate, the pH should ideally be below 4.0 to prevent drug precipitation in the event the solution is exposed to a low temperature.

To confirm that they could be made isotonic without affecting drug stability, sodium chloride (Sigma, Poole, UK) was added to the zolpidem solutions that remained clear after two weeks storage. Approximately 33 mg, 30 mg and 24 mg of sodium chloride was added to the 10 mg/ml, 15 mg/ml and 20 mg/ml zolpidem solutions, respectively and the solutions stirred until the sodium chloride had dissolved. All solutions remained clear and their osmolality values are presented in Table 4.

TABLE 4

Characteristics of cyclodextrin-free zolpidem tartrate solutions

| Formulation | pH | Osmolality following addition of NaCl (osmol/kg) | Appearance after storage at 2-8° C. for 2 weeks |
|---|---|---|---|
| 20 mg/ml zolpidem tartrate + 5 mg/ml chitosan glutamate | 4.0 | — | White precipitate |
| 20 mg/ml zolpidem tartrate + 5 mg/ml chitosan glutamate | 3.5 | 0.273 | Clear colourless solution |
| 15 mg/ml zolpidem tartrate + 5 mg/ml chitosan glutamate | 4.0 | — | White precipitate |
| 15 mg/ml zolpidem tartrate + 5 mg/ml chitosan glutamate | 3.5 | 0.296 | Clear colourless solution |
| 10 mg/ml zolpidem tartrate + 5 mg/ml chitosan glutamate | 4.0 | 0.275 | Clear colourless solution |
| 10 mg/ml zolpidem tartrate + 5 mg/ml chitosan glutamate | 3.5 | 0.290 | Clear colourless solution |

The invention claimed is:

1. A composition in the form of an aqueous solution for nasal delivery of zolpidem or a pharmaceutically acceptable salt thereof, wherein the composition consists essentially of:
   (a) 16 to 97 mg/ml of zolpidem (expressed as the free base);
   (b) 50 to 400 mg/ml of sulfobutylether β-cyclodextrin (SBE-CD); and
   (c) 1 to 20 mg/ml of chitosan, a salt, or a derivative thereof formed by bonding acyl and/or alkyl groups with the hydroxyl groups, but not the amino groups of chitosan or a salt of the derivative thereof; and
   wherein the composition has a pH of 3.5 to 5.6 and a viscosity of less than 150 cp.

2. The composition according to claim 1, wherein component (a) is a salt of zolpidem selected from the hydrochloride, mesilate, citrate, nitrate, lactate, maleate, tartrate, phosphate, succinate, fumarate and gluconate salts.

3. The composition according to claim 2, wherein the salt is the tartrate salt.

4. The composition according to claim 1, wherein the zolpidem (expressed as the free base) is present in a concentration of from 24 to 80 mg/ml.

5. The composition according to claim 1, comprising wherein the SBE-CD is present in a concentration of 100 to 400 mg/ml.

6. The composition according to claim 1, wherein the composition is an aqueous solution and consists essentially of from 30 to 60 mg/ml of zolpidem tartrate, 100 to 300 mg/ml SBE-CD and 2 to 10 mg/ml of chitosan glutamate.

7. A method of administering zolpidem or a pharmaceutically acceptable salt thereof to a patient in need thereof, which method comprises the intranasal administration of a composition as defined in claim 1.

8. A method of treating insomnia, which method comprises the intranasal administration of a composition as defined in claim 1.

9. A method of treating a neurological disorder or Parkinson's disease, which method comprises the intranasal administration of a composition as defined in claim 1.

10. A method according to claim 9, wherein the neurological disorder is one arising from brain trauma, stroke or spinocerebellar ataxia.

* * * * *